United States Patent [19]

Seeger et al.

[11] 3,997,589

[45] Dec. 14, 1976

[54] 4-(2'-FLUORO-4-BIPHENYLYL)-4-OXO-BUTYRIC ACID AND ESTERS AND SALTS THEREOF

[75] Inventors: Ernst Seeger; Wolfhard Engel; Josef Nickl; Helmut Teufel, all of Biberach an der Riss, Germany

[73] Assignee: Boehringer Ingelheim GmbH, Ingelheim am Rhein, Germany

[22] Filed: Jan. 23, 1975

[21] Appl. No.: 543,266

Related U.S. Application Data

[63] Continuation-in-part of Ser. No. 234,346, March 13, 1972, abandoned.

[30] Foreign Application Priority Data

Mar. 17, 1971 Germany .......................... 2112716
Mar. 17, 1971 Germany .......................... 2112715
Mar. 17, 1971 Germany .......................... 2112840

[52] U.S. Cl. .................. 260/469; 260/247.2 R; 260/483; 260/501.16; 260/515 A; 260/539 R; 260/649 F

[51] Int. Cl.² .................. C07C 65/20; C07C 69/76

[58] Field of Search ......... 260/515 A, 469, 501.16, 260/247.2 R; 424/308, 317, 316

[56] References Cited

UNITED STATES PATENTS

| | | | |
|---|---|---|---|
| 3,120,551 | 2/1964 | Goldschmidt | 260/455 |
| 3,754,021 | 8/1973 | Shen et al. | 260/515 A |
| 3,867,434 | 2/1975 | Diamond | 260/515 A |

FOREIGN PATENTS OR APPLICATIONS

56/65  2/1965  Ireland .......................... 260/515 A

*Primary Examiner*—Jane S. Myers
*Attorney, Agent, or Firm*—Hammond & Littell

[57] ABSTRACT

Compounds of the formula

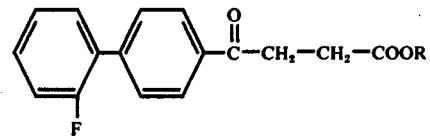

wherein R is hydrogen or alkyl of 1 to 4 carbon atoms, and, when R is hydrogen, non-toxic salts thereof formed with an inorganic or organic base; the compounds as well as the salts are useful as antiphlogistics and antiproliferatives.

12 Claims, No Drawings

4-(2'-FLUORO-4-BIPHENYLYLR-4-OXO-BUTYRIC ACID AND ESTERS AND SALTS THEREOF

This is a continuation-in-part of copending application Ser. No. 234,346, filed Mar. 13, 1972, now abandoned.

This invention relates to a novel class of compounds represented by the formula

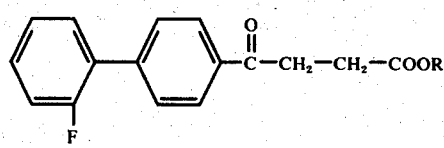
(I)

wherein R is hydrogen or alkyl of 1 to 4 carbon atoms, and, when R is hydrogen, non-toxic salts thereof formed with an inorganic or organic base.

The compounds embraced by formula I above may be prepared by acylating 2-fluoro-biphenyl of the formula

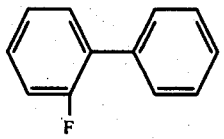
(II)

with succinic acid anhydride or an alkyl succinate halide of the formula

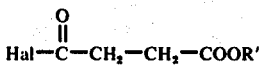
(III)

wherein
R' is alkyl of 1 to 4 carbon atoms and
Hal is chlorine, bromine or iodine,
in the presence of a Lewis acid and of a solvent.

The acylation reaction is advantageously performed at a temperature between 0° and 80° C. The solvent medium may be any solvent conventionally used for such acylation reactions, for instance nitrobenzene, carbon disulfide or chlorinated hydrocarbons, such as methylene chloride, ethylene chloride or trichloroethylene or mixtures of these. Examples of suitable Lewis acids are anhydrous aluminum chloride, borontrifluoride, anhydrous iron-III-chloride, tin tetrachloride or anhydrous zinc chloride.

After completion of the reaction, the reaction mixture is worked up in a manner conventional for Friedel-Crafts reaction mixtures, such as by stirring the reaction mixture into a mixture of ice and hydrochloric acid.

In those instances where this method yields a compound of the formula I wherein R is alkyl, the same may, if desired, be converted into the corresponding free oxobutyric acid (R = H) by acid or alkaline hydrolysis.

The starting compound of the formula II, i.e. 2-fluoro-biphenyl, m.p. 73° C, was prepared from the corresponding 2-amino-biphenyl by thermal decomposition of the intermediately formed diazonium-tetrafluoroborate [cf. also G. Schieman and W. Roselius, Berichte 62, 1805 (1929); or the summary by A. Roe, Org. Reactions V, 193–228, J. Wiley and Sons, New York (1949)].

The starting compounds of the formula III may, for example, be prepared by reacting a succinic acid monoester with phosphorus trichloride, phosphorus pentachloride or thionyl chloride.

The free carboxylic acid (R = H) of the formula I obtained by the above-described method may, if desired, be converted into a corresponding alkyl ester (R = alkyl) by conventional esterification procedures, and preferably by esterification in the presence of a strong acid, such as concentrated sulfuric acid, with the desired alkanol.

Conversely, if the above-described method yields a compound of the formula I wherein R is alkyl, this ester group may readily be split off by acid or alkaline hydrolysis. For instance, the free acid may be obtained by briefly heating the ester with methanolic potassium hydroxide, and acidifying the reaction mixture.

Finally, the compound of the formula I wherein R is hydrogen may, if desired, be converted by conventional methods into a non-toxic, pharmacologically acceptable alkali metal or alkaline earth metal salt thereof, or into an addition salt thereof with an organic base, such as cyclohexylamine, isobutylamine, morpholine, ethanolamine, diethanolamine, dimethylaminoethanol or the like.

The following examples illustrate the present invention and will enable others skilled in the art to understand it more completely. It should be understood, however, that the invention is not limited solely to the particular examples given below.

EXAMPLE 1

4-(2'-Fluoro-4-biphenylyl)-4-oxo-butyric acid and various amine salts thereof 286 gm (2.14 mol) of aluminum chloride were added in small portions to a solution of 123.2 gm (0.716 mol) of 2-fluoro-biphenyl (m.p. 72° C) and 71.6 gm (0.716 mol) of succinic acid anhydride in 1200 cc of methylene chloride which had been cooled to 0° C, accompanied by stirring and taking care that the temperature of the mixture did not rise above +5° C. After all of the aluminum chloride had been added, the reaction mixture was stirred for 5 hours more at room temperature and was then poured into a mixture of 5 liters of ice water and 500 cc of concentrated hydrochloric acid. The precipitate formed thereby was collected by vacuum filtration, washed first with water and then with 500 cc of ether, and then dissolved in 2.5 liters of ethyl acetate. The solution was treated with charcoal and filtered. The resulting solution was evaporated to a volume of 800 cc and allowed to cool. The crystals which separated out (94 gm; m.p. 161°–162° C) were collected, and the filtrate was evaporated to 1/3 its volume, whereby an additional 37 gm of the crystalline product (m.p. 160°–161° C) separated out, giving a total yield of 131 gm (67.3% of theory) of the compound of the formula

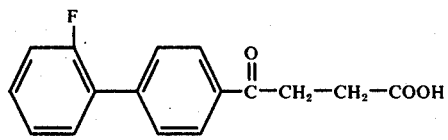

The isobutylamine salt of the free acid, which was precipitated from ethyl acetate and recrystallized from ethyl acetate/absolute ethanol, had a melting point of 130° C.

The diethanolamine salt, m.p. 93°–94° C, was obtained by dissolving the free acid in acetone, adding the calculated equivalent amount of diethanolamine to the solution, then adding ethyl acetate until the solution became turbid, allowing the turbid mixture to stand, and recrystallizing the precipitate formed thereby from acetone.

The cyclohexylamine salt obtained in analogous fashion had a melting point of 147°–149° C.

The morpholine salt had a melting point of 126°–127° C.

EXAMPLE 2

4-(2'-Fluoro-4-biphenylyl)-4-oxo-butyric acid and various lower alkyl esters thereof 26.6 gm (0.2 mol) of powdered aluminum chloride were introduced over a period of 15 minutes into a mixture consisting of 17.2 gm (0.1 mol) of 2-fluorobiphenyl, 16.4 gm (0.1 mol) of ethyl succinate chloride and 200 ml of ethylene chloride at 10° C, accompanied by stirring, and the resulting mixture was heated for 3 hours at 60° C. Thereafter, the reaction mixture was allowed to stand for several hours at room temperature, was then poured into a mixture of ice and hydrochloric acid, and 200 ml of ether were added to the mixture. The organic phase was separated, washed with water, with aqueous sodium bicarbonate and again with water, dried over sodium sulfate, and the solvent was distilled off. The oily residue was distilled in vacuo, yielding 23.1 gm (77% of theory) of ethyl 4-(2'-fluoro-4-biphenylyl)-4-oxo-butyrate, b.p. 190°–192° C at 0.4 mm Hg, which solidified into a crystalline substance after standing for some time and had a melting point of 56°–58° C after recrystallization from petroleum ether.

In analogous manner, propyl 4-(2'-fluoro-4-biphenylyl)-4-oxo-butyrate, m.p. 53°–54° C (from petroleum ether), was obtained by using propyl succinate chloride.

Methyl 4-(2'-fluoro-4-biphenylyl)-4-oxo-butyrate, m.p. 78°–79° C (from methanol), was obtained by using methyl succinate chloride.

Hydrolysis of the above esters with ethanolic 20% potassium hydroxide in conventional manner yielded free 4-(2'-fluoro-4-biphenylyl)-4-oxo-butyric acid, m.p. 160°–161° C.

EXAMPLE 3

Isopropyl 4-(2'-fluoro-4-biphenylyl)-4-oxo-butyrate

Prepared analogous to Example 2 from 2-fluorobiphenyl and isopropyl succinate chloride. Melting point 65°–66° C (from cyclohexane/petroleum ether).

The compounds according to the present invention, that is, those embraced by formula I above and the non-toxic salts of the free acid, have useful pharmacodynamic properties. More particularly, they exhibit antiphlogistic, analgesic, antitussive and thrombocyte aggregation inhibiting activities in warm-blooded animals, such as mice and rats. With respect to the antiphlogistic activity, the compounds of the present invention are significantly superior to known antiphlogistics of similar structure in that their antiphlogistic action is of exceptionally long duration.

The antiphlogistic activity of the compounds of the present invention, as well as the antiphlogistic activity of certain closely related compounds disclosed in U.S. Pat. No. 3,120,551 and French Pat. No. 1,430,359 was determined by the method described below, and the following are illustrative results of these tests, where A = 4-(2'-fluoro-4-biphenylyl)-4-oxo-butyric acid, described in Example 1 of the present application;

B = 5-(4-biphenylyl)-3-methyl-5-oxo-valeric acid, disclosed in Col. 3 (Example 1), line 54, of U.S. Pat. No. 3,120,551 to Goldschmidt;

C = 5-(4-biphenylyl)-3-methyl-valeric acid, disclosed in Col. 3 (Example 1), lines 74–75, of U.S. Pat. No. 3,120,551;

D = 5-(2'-fluoro-4-biphenylyl)-5-oxo-valeric acid, disclosed in French Pat. No. 1,430,359;

E = ethyl 3-(2'-fluoro-4-biphenylyl)-3-oxo-propionate, disclosed in French Pat. No. 1,430,359; and F = 3-(2'-fluoro-4-biphenylyl)-3-oxo-propionic acid, disclosed in French Pat. No. 1,430,359.

1. Antiphlogistic Activity

The compounds were tested for their anti-exudative effects on the kaolin edema of the hind paw of the rat.

The kaolin edema was induced according to the method of Hillebrecht [Arzneimittel-Forsch. 4, 607 (1954)] by subplantary injection of 0.05 ml of a 10% suspension of kaolin in a 0.85% sodium chloride solution. The measurement of the thickness of the paws was done by using the technique of Doepfner and Cerletti [Int. Arch. Allergy. Immonol. 12, 89 (1958)].

Male FW 49-rats of an average weight of 120–150 gm were orally treated with the test compound with the aid of an esophageal tube 30 minutes before inducement of the edema. Five hours after the provocation of the edema the averaged values of the swelling caused in the paws of the rats treated with the test compound were compared with those values measured on blind-treated control animals. By graphic extrapolation, the dose leading to a 35% reduction of the swelling ($ED_{35}$) was calculated from the percent reduction values measured by administration of different doses.

The following table shows the results obtained from the above tests:

| Compound | $ED_{35}$ kaolin edema mgm/kg p.o. |
|---|---|
| Invention: | |
| A | 13 |
| Prior art: | |
| B | 450 |
| C | 230 |
| D | 98 |
| E | 80 |
| F | 79 |

The analgesic activity of the compounds of the instant invention was ascertained by means of the writhing test.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 6.7 mgm/kg, preferably 1.3 to 5.0 mgm/kg body weight, and the daily dose rate is 1.6 to 16.7 mgm/kg. body weight. The single effective antiphlogistic dose for compound A above is about 2.1 mgm/kg and the effective daily dose rate is about 6.5 mgm/kg, whereas the corresponding single and daily dosage range for prior art compounds D and E are 10–13.5 mgm/kg and 30–40 mgm/kg, respectively.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 4

Tablets

The tablet composition is compounded from the following ingredients:

| | |
|---|---|
| 4-(2'-Fluoro-4-biphenylyl)-4-oxo-butyric acid | 200.0 parts |
| Corn starch | 97.0 parts |
| Polyvinylpyrrolidone | 10.0 parts |
| Magnesium stearate | 3.0 parts |
| Total | 310.0 parts |

Preparation

The butyric acid compound is admixed with the corn starch, the mixture is granulated with an aqueous 14% solution of the polyvinylpyrrolidone through a 1.5 mm-mesh screen, the granulate is dried at 45° C and again passed through the screen, the dry granulate is admixed with the magnesium stearate, and the composition is compressed into 310 mgm-tablets with the aid of a conventional tablet making machine. Each tablet contains 200 mgm of the butyric acid compound and is an oral dosage unit composition with effective antiphlogistic action.

EXAMPLE 5

Coated pills

The pill core composition is compounded from the following ingredients:

| | |
|---|---|
| 4-(2'-Fluoro-4-biphenylyl)-4-oxo-butyric acid | 300.0 parts |
| Corn starch | 70.0 parts |
| Gelatin | 8.0 parts |
| Talcum | 18.0 parts |
| Magnesium stearate | 4.0 parts |
| Total | 400.0 parts |

Preparation

The butyric acid compound is admixed with the corn starch, the mixture is granulated with an aqueous 10% solution of the gelatin through a 1.5 mm-mesh screen, the granulate is dried at 45° C and again passed through the screen, the dry granulate is admixed with the talcum and the magnesium stearate, and the composition is compressed into 400 mgm-pill cores. These cores are subsequently coated in conventional manner with a thin shell consisting essentially of a mixture of talcum and sugar, and finally polished with beeswax. Each coated pill contains 300 mgm of the butyric acid compound and is an oral dosage unit composition with effective antiphlogistic action.

EXAMPLE 6

Gelatin capsules

The capsule filler composition is compounded from the following ingredients:

| | |
|---|---|
| 4-(2'-Fluoro-4-biphenylyl)-4-oxo-butyric acid | 200.0 parts |
| Corn starch | 190.0 parts |
| Colloidal silicic acid | 6.0 parts |
| Magnesium stearate | 4.0 parts |
| Total | 400.0 parts |

Preparation

The ingredients are intimately admixed with each other, and 400 mgm-portions of the mixture are filled into No. 1 gelatin capsules. Each capsule contains 200 mgm of the butyric acid compound and is an oral dosage unit composition with effective antiphlogistic action.

EXAMPLE 7

Suppositories

The suppository composition is compounded from the following ingredients:

| | |
|---|---|
| 4-(2'-Fluoro-4-biphenylyl)-4-oxo-butyric acid | 300.0 parts |
| Suppository base (e.g. cocoa butter) | 1450.0 parts |
| Total | 1750.0 parts |

Preparation

The finely pulverized butyric acid compound is homogeneously blended with the aid of an immersion homogenizer into the suppository base which has previously been melted and cooled to 40° C. 1750 mgm-portions of the mixture are poured at 37° C into cooled suppository molds and allowed to harden therein. Each suppository contains 300 mgm of the butyric acid compound and is a rectal dosage unit composition with effective antiphlogistic action.

EXAMPLE 8

Hypodermic solution

The solution is compounded from the following ingredients:

| | | |
|---|---|---|
| 4-(2'-Fluoro-4-biphenylyl)-4-oxo-butyric acid | | 150.0 parts |
| 1N Sodium hydroxide | q.s.ad | pH 9.0 |
| Distilled water | q.s.ad | 3000.0 parts by vol. |

Preparation

The butyric acid compound is suspended in a sufficient amount of distilled water and caused to go into solution by addition of the sodium hydroxide until pH 9. The solution is diluted to the indicated volume with additional distilled water, filtered until free from suspended particles, and the filtrate is filled into 3 ml-ampules which are sterilized for 20 minutes at 120° C and then sealed. Each ampule contains 150 mgm of the butyric acid compound, and the contents thereof are an injectable dosage unit composition with effective antiphlogistic action.

EXAMPLE 9

Suspension

The suspension is compounded from the following ingredients:

| | |
|---|---|
| 4-(2'-Fluoro-4-biphenylyl)-4-oxo-butyric acid | 4.0 parts |
| Dioctyl sodium sulfosuccinate (DONSS) | 0.02 parts |
| Benzoic acid | 0.1 parts |
| Sodium cyclamate | 0.2 parts |
| Colloidal silicic acid | 1.0 parts |
| Polyvinylpyrrolidone | 0.1 parts |
| Glycerin | 25.0 parts |
| Grapefruit flavoring | 0.1 parts |
| Distilled water q.s.ad | 100.0 parts by vol. |

Preparation

A sufficient amount of distilled water is heated to 70° C, and the DONSS, the benzoic acid, the sodium cyclamate and the polyvinylpyrrolidone are successively dissolved therein. The glycerin and the colloidal silicic acid are added to the solution, and the finely pulverized butyric acid compound is suspended in the mixture with the aid of an immersion homogenizer. Finally, the flavoring is added and the suspension is diluted to the indicated volume with distilled water. 5 ml of the suspension contain 200 mgm of the butyric acid compound and are an oral dosage unit composition with effective antiphlogistic action.

Analogous results are obtained when any one of the other compounds embraced by formula I, or a non-toxic salt of the free acid, is substituted for the particular butyric acid compound in Examples 4 through 9. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

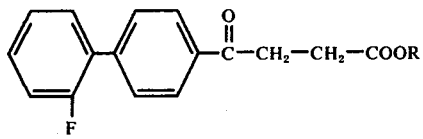

wherein R is hydrogen or alkyl of 1 to 4 carbon atoms, or, when R is hydrogen, a non-toxic salt thereof formed with an inorganic or organic base.

2. A compound of claim 1, which is 4-(2'-fluoro-4-biphenylyl)-4-oxo-butyric acid or a non-toxic salt thereof formed with an inorganic or organic base.

3. The compound of claim 1 which is 4-(2'-fluoro-4-biphenylyl)-4-oxo-butyric acid.

4. The compound of claim 1 which is ethyl 4-(2'-fluoro-4-biphenylyl)-4-oxo-butyrate.

5. The compound of claim 1 which is propyl 4-(2'-fluoro-4-biphenylyl)-4-oxo-butyrate.

6. The compound of claim 1 which is methyl 4-(2'-fluoro-4-biphenylyl)-4-oxo-butyrate.

7. The compound of claim 1 which is the isobutylamine salt of 4-(2'-fluoro-4-biphenylyl)-4-oxo-butyric acid.

8. The compound of claim 1 which is the diethanolamine salt of 4-(2'-fluoro-4-biphenylyl)-4-oxo-butyric acid.

9. The compound of claim 1 which is the cyclohexylamine salt of 4-(2'-fluoro-4-biphenylyl)-4-oxo-butyric acid.

10. The compound of claim 1 which is the morpholine salt of 4-(2'-fluoro-4-biphenylyl)-4-oxo-butyric acid.

11. A pharmaceutical dosage unit composition consisting essentially of an inert pharmaceutical carrier and an effective antiphlogistic amount of a compound according to claim 1.

12. The method of counteracting inflammation and fever in a warm-blooded animal, which comprises administering to said animal an effective antiphlogistic amount of a compound according to claim 1.

* * * * *